United States Patent
Xie et al.

(10) Patent No.: US 9,696,438 B2
(45) Date of Patent: Jul. 4, 2017

(54) PET DETECTION STRUCTURE AND SYSTEM WITH APPLICATION ADAPTABILITY

(71) Applicant: RAYCAN TECHNOLOGY CO., LTD. (SU ZHOU), Suzhou New District, Suzhou, Jiangsu (CN)

(72) Inventors: Qingguo Xie, Jiangsu (CN); Jingjing Liu, Jiangsu (CN); Luyao Wang, Jiangsu (CN); Jun Zhu, Jiangsu (CN)

(73) Assignee: RAYCAN TECHNOLOGY CO., LTD. (SU ZHOU), Suzhou New District, Suzhou, Jiangsu (CN)

( * ) Notice: Subject to any disclaimer, the term of this patent is extended or adjusted under 35 U.S.C. 154(b) by 0 days.

(21) Appl. No.: 14/764,935

(22) PCT Filed: Mar. 25, 2013

(86) PCT No.: PCT/CN2013/073125
§ 371 (c)(1),
(2) Date: Jul. 30, 2015

(87) PCT Pub. No.: WO2014/121547
PCT Pub. Date: Aug. 14, 2014

(65) Prior Publication Data
US 2015/0355344 A1 Dec. 10, 2015

(30) Foreign Application Priority Data
Feb. 5, 2013 (CN) .......................... 2013 1 0045927

(51) Int. Cl.
*G01T 1/29* (2006.01)
*G01T 1/16* (2006.01)
(Continued)

(52) U.S. Cl.
CPC ............ *G01T 1/2985* (2013.01); *A61B 6/037* (2013.01); *G01T 1/161* (2013.01); *G01T 1/1644* (2013.01)

(58) Field of Classification Search
CPC ..... A61B 6/4411; A61B 6/037; G01T 1/2985; G01T 1/1644; G01T 1/1603; G01T 1/249; G01T 1/161; G01T 1/243
(Continued)

(56) References Cited

U.S. PATENT DOCUMENTS 7,049,600 B2 * 5/2006 Levin .................... G01T 1/2018
250/363.04
7,626,389 B2 * 12/2009 Fiedler ................... G01R 33/28
324/307
(Continued)

FOREIGN PATENT DOCUMENTS

CN 101856236 A 10/2010
CN 101990643 A 3/2011
(Continued)

OTHER PUBLICATIONS

Jingjing, Liu, et al., An investigation of local high spatial resolution adaptive PET system, China Engineering Science, vol. 13, No. 10, p. 106-108, Dec. 31, 2011.
(Continued)

*Primary Examiner* — Mark R Gaworecki
(74) *Attorney, Agent, or Firm* — Knobbe Martens Olson & Bear LLP

(57) ABSTRACT

A PET detection structure with application adaptability includes: at least two detector blocks and a detection ring for disposing the detector blocks. The at least two detector blocks are placed on the detection ring and surround a detected object in a manner of encirclement. The performance of each detector block includes inherent spatial
(Continued)

resolution, time behavior, energy resolution, detection efficiency and maximum counting rate. The performance of the detector blocks are divided into a plurality of performance levels, and the performance level of one performance of at least one detector block of the at least two detector blocks is higher than the performance rate of the same performance of the other detector blocks.

12 Claims, 3 Drawing Sheets

(51) Int. Cl.
  *G01T 1/164* (2006.01)
  *G01T 1/161* (2006.01)
  *A61B 6/03* (2006.01)
(58) Field of Classification Search
  USPC .................................................. 250/363.03
  See application file for complete search history.

(56) References Cited

U.S. PATENT DOCUMENTS

| | | | | |
|---|---|---|---|---|
| 8,378,305 B2* | 2/2013 | Gagnon | ................ | A61B 6/037 250/362 |
| 8,664,611 B2* | 3/2014 | Xie | ................ | A61B 6/037 250/252.1 |
| 2008/0128626 A1* | 6/2008 | Rousso | ................ | A61B 5/418 250/362 |
| 2008/0230704 A1 | 9/2008 | Daghighian | | |
| 2008/0284428 A1* | 11/2008 | Fiedler | ................ | G01R 33/28 324/307 |
| 2009/0159804 A1* | 6/2009 | Shibuya | ................ | G01T 1/2985 250/363.03 |
| 2009/0250616 A1* | 10/2009 | Solf | ................ | G01T 1/2985 250/363.04 |
| 2010/0187424 A1* | 7/2010 | Majewski | ................ | A61B 6/037 250/363.05 |
| 2010/0264320 A1 | 10/2010 | Takayama et al. | | |
| 2011/0024636 A1* | 2/2011 | Gagnon | ................ | G01T 1/2985 250/362 |
| 2011/0062340 A1* | 3/2011 | Gagnon | ................ | G01T 1/1644 250/363.03 |
| 2012/0091348 A1* | 4/2012 | Wang | ................ | G01T 1/2018 250/362 |
| 2012/0267536 A1* | 10/2012 | Gagnon | ................ | G01T 1/1644 250/363.03 |
| 2012/0267537 A1* | 10/2012 | Gagnon | ................ | A61B 6/037 250/363.03 |
| 2012/0271164 A1* | 10/2012 | Gagnon | ................ | A61B 6/037 600/427 |
| 2013/0087697 A1* | 4/2013 | Xie | ................ | A61B 6/037 250/252.1 |

FOREIGN PATENT DOCUMENTS

| | | |
|---|---|---|
| CN | 102178542 A | 9/2011 |
| CN | 202151361 U | 2/2012 |
| EP | 2581043 A1 | 4/2013 |
| WO | 2011/157045 A1 | 12/2011 |

OTHER PUBLICATIONS

Office Action issued Jul. 26, 2016 in corresponding JP application No. 2015-555538.
Office Action issued Aug. 5, 2015 in corresponding CN application No. 201310045927.2.
Extended European Search Report issued Aug. 26, 2016 in corresponding EP Application No. 13874369.5.

* cited by examiner

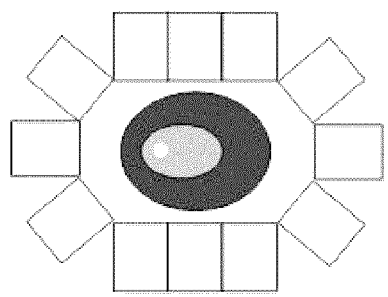
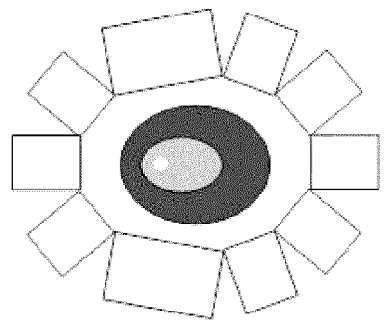
Fig.4(a)  Fig.4(b)
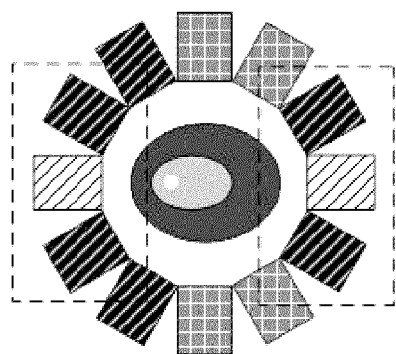
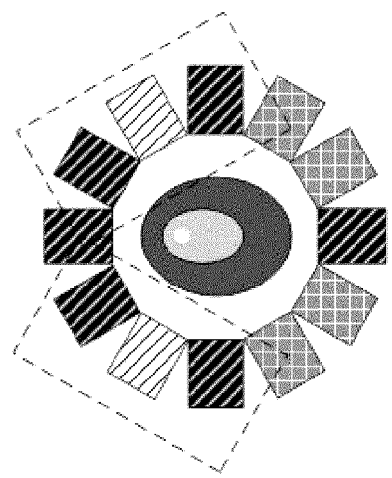
Fig.5(a)  Fig.5(b)

PET DETECTION STRUCTURE AND SYSTEM WITH APPLICATION ADAPTABILITY

The present application is the national phase of International Application No. PCT/CN2013/073125, titled "PET DETECTION STRUCTURE AND SYSTEM WITH APPLICATION ADAPTABILITY", filed on Mar. 25, 2013, which claims the priority Chinese Patent Application No. 201310045927.2, entitled "PET DETECTION STRUCTURE AND SYSTEM WITH APPLICATION ADAPTABILITY", filed on Feb. 5, 2013 with the State Intellectual Property Office of People's Republic of China, both of which are incorporated herein by reference in entirety.

FIELD

The present disclosure relates to the technical field of position emission tomography (PET), and in particular to a PET detection structure and system with application adaptability.

BACKGROUND

Positron Emission Tomography (hereinafter referred to as PET for short) is a non-invasive imaging method which can non-invasively, quantitatively and dynamically assess the metabolism, biochemical reactions, functional activities and perfusion of various organs of human body. Therefore, PET is used for early diagnosis and analysis of tumors, cardiac diseases and neurological diseases and plays a unique role in the prevention and treatment of serious diseases. During a PET imaging, it is needed to inject a drug marked with radioisotopes into a human body, an animal or an organism under detection. In the tissue of the object under detection, these radioisotopes encounter electrons and annihilate to generate a pair of $\gamma$ photons. A detector at the periphery of the object under detection receives the $\gamma$ photons and converts them into electrical signals. A series of processes are performed on these electrical signals, and an activity distribution of the object under detection is obtained by image reconstruction.

PET imager mainly includes a detector block, an electronics module and an image reconstruction module. The detector block receives and deposits $\gamma$ photons and converts the $\gamma$ photons into electrical signals; the electronics module processes and transmits these electrical signals; the image reconstruction module processes the signal obtained by the system to obtain an image of activity distribution of the object under detection.

The existing PETs are designed in a universal mode and pursue the improvement of overall performance in the field of view, all detector blocks have almost identical performance, besides, same configuration and layout are used for all objects under detection. However, in most cases, imaging with relatively high quality is only required for a certain region of interest. If the whole PET detection system is updated or upgraded to meet performance requirement with respect to a certain region of interest, there will be wasted and spare capacities in other regions. Furthermore, being constrained by the cost, it is impossible for the PET constructed in this way to use only detector blocks with extremely high performance, therefore extremely high imaging quality can not be obtained.

Therefore, in view of the technical problems, it is necessary to provide a PET detection structure and system with improved structure and application adaptability to overcome foregoing shortcomings.

SUMMARY

In view of this, the disclosure is to provide a PET detection structure and system with application adaptability. While ensuring acquirement of high quality images in a local region, the PET detection structure and system with application adaptability reduces the used amount of detector blocks of high performance level, and saves cost for establishing the system.

For this purpose, technical solutions are provided as follows.

A PET detection structure with application adaptability, includes at least two detector blocks and a detection ring for disposing the detector blocks, the at least two detector blocks are arranged on the detection ring and surround an object under detection. Each detector block has properties including inherent spatial resolution, temporal characteristic, energy resolution, detection efficiency and a maximum counting rate. The properties of the detector block are graded into a plurality of levels, and at least one detector block in the at least two detector blocks has a higher level than other detector blocks in terms of a same property.

Preferably, in the PET detection structure with application adaptability, the surrounding is in a regular geometric shape, or in an irregular convex shape, or in a geometric shape similar to that of the object under detection according to structural characteristic of the object under detection.

Preferably, in the PET detection structure with application adaptability, the levels of the detector blocks are graded with an equal interval, where the interval between the levels of the inherent spatial resolution is in a range of 0.1 mm-10.0 mm, the interval between the levels of the temporal characteristic is in a range of 10 ps-50 ns, the interval between the levels of the energy resolution is in a range of 3%-50%, the interval between the levels of the detection efficiency is in a range of 3%-90%, and the interval between the levels of the maximum counting rate is in a range of 10 k cps-20M cps.

Preferably, in the PET detection structure with application adaptability, the properties of the detector block are graded into two levels by a fixed value, where the fixed value for grading levels of the inherent spatial resolution is in a range of 0.1 mm-10.0 mm, the fixed value for grading levels of the temporal characteristic is in a range of 10 ps-50 ns, the fixed value for grading levels of the energy resolution is in a range of 3%-50%, the fixed value for grading levels of the detection efficiency is in a range of 3%-90%, and the fixed value for grading levels of the maximum counting rate is in a range of 10 k cps-20 M cps.

Preferably, in the PET detection structure with application adaptability, in a case that a difference between optimal performance and worst performance of all the detector blocks is greater than a threshold, it is determined that a level difference for the property is present, where the threshold for determining the presence of level difference for the inherent spatial resolution is in a range of 0.1 mm-10.0 mm, the threshold for determining the presence of level difference for the temporal characteristic is in a range of 10 ps-50 ns, the threshold for determining the presence of level difference for the energy resolution is in a range of 3%-50%, the threshold for determining the presence of level difference for the detection efficiency is in a range of 3%-90%, and the threshold for determining the presence of level difference for the maximum counting rate is in a range of 10 k cps-20 M cps.

Preferably, in the PET detection structure with application adaptability, the levels of the detector blocks are graded with an equal interval, where the interval between the levels of the inherent spatial resolution is in a range of 0.1 mm-10.0 mm, the interval between the levels of the temporal characteristic is in a range of 10 ps-50 ns, the interval between the levels of the energy resolution is in a range of 3%-50%, the interval between the levels of the detection efficiency is in a range of 3%-90%, and the interval between the levels of the maximum counting rate is in a range of 10 k cps-20 M cps.

Preferably, in the PET detection structure with application adaptability, the properties of the detector block are graded into two levels by a fixed value, where the fixed value for grading levels of the inherent spatial resolution is in a range of 0.1 mm-10.0 mm, the fixed value for grading levels of the temporal characteristic is in a range of 10 ps-50 ns, the fixed value for grading levels of the energy resolution is in a range of 3%-50%, the fixed value for grading levels of the detection efficiency is in a range of 3%-90%, and the fixed value for grading levels of the maximum counting rate is in a range of 10 k cps-20 M cps.

Preferably, in the PET detection structure with application adaptability, the detector blocks are arranged base on one of the five kinds of properties in the following ways:

(1) The detector blocks with a same level or with adjacent levels or with a plurality of different levels are arranged in an equally spaced way.

(2) The detector blocks with a same level or with adjacent levels or with a plurality of different levels are arranged in a way that sections of the detector blocks are clustered into a single aggregation or a plurality of aggregations Preferably, in the PET detection structure with application adaptability, each of the plurality of aggregations functions as one detecting unit, the plurality of detecting units are arranged on the detection ring in a symmetric way, in a way that some are closely arranged and some are distributed, or in a spaced way.

Preferably, in the PET detection structure with application adaptability, the detector blocks are arranged based on at least two of the five kinds of properties in the following ways.

(1) Detector blocks with an arbitrary level or with adjacent levels or with a plurality of different levels in terms of the plurality of properties are clustered as one detecting unit, and the detecting units are arranged in a spaced way.

(2) Detector blocks with an arbitrary level or with adjacent levels or with a plurality of different levels in terms of the plurality of properties are clustered as one detecting unit, and the detecting units are arranged in a way that sections of the detector blocks are clustered into a single aggregation or a plurality of aggregations.

Preferably, in the PET detection structure with application adaptability, the plurality of detecting units are arranged on the detection ring in a symmetric way, in a way that some are closely arranged and some are distributed, or in a spaced way.

A PET detection system with application adaptability includes any one of the positron emission tomography detection structure with application adaptability as described above, a detector controlling module, an image reconstruction module and a detector programming module.

It is can be seen from the technical solutions that in the PET detection structure and system with application adaptability according to the embodiments of the disclosure, detector blocks of different performance levels cooperate with each other; besides, by optimizing the arrangement of the detector blocks, the used amount of detector blocks of high performance level is reduced while ensuring quality of the acquired images, and cost for establishing the system is saved.

BRIEF DESCRIPTION OF THE DRAWINGS

The appended drawings to be used in the description of the embodiments and the conventional technology will be described briefly as follows, so that the technical solutions according to the embodiments of the present disclosure or according to the conventional technology will become clearer. It is obvious that the appended drawings in the following description only illustrate some embodiments of the present disclosure. For those skilled in the art, other appended drawings may be obtained according to these appended drawings without any creative work.

FIG. 2(a) is a schematic diagram in which detector blocks with same size are distributed in a regular circle in an equally spaced way; FIG. 2(b) is a schematic diagram in which a radius of the detecting system is changed and detector blocks are closely arranged in a circle; FIG. 2(c) is a schematic diagram in which detector blocks are closely arranged in an oval; FIG. 2(d) is a schematic diagram in which detector blocks are closely arranged in half arcs with two ends opened;

FIG. 3(a) is a schematic diagram in which detector blocks are arranged on the detection ring in the way that the level 3 detector blocks are equally spaced; FIG. 3(b) is a schematic diagram in which detector blocks are arranged on the detection ring in the way that the level 1 and level 2 detector blocks are equally spaced; FIG. 3(c) is a schematic diagram in which detector blocks are arranged on a detection ring in the way that the level 1 and level 2 detector blocks are unequally spaced; FIG. 3(d) is a schematic diagram in which detector blocks are arranged on a detection ring in the way that the level 1 and level 3 detector blocks are unequally spaced; FIG. 3(e) is a schematic diagram in which detector blocks are arranged on a detection ring in the way that the level 1, level 2 and level 3 detector blocks are circularly arranged; FIG. 3(f) is a schematic diagram in which detector blocks are arranged on a detection ring in a way that the level 1, level 2 and level 3 detector blocks are clustered into a single aggregation or a plurality of aggregations; and FIG. 3(g) is a schematic diagram in which detector blocks are arranged on a detection ring in a way that the level 1 and level 2 detector blocks are clustered into a single aggregation or in a way that the level 2 and level 3 detector blocks are clustered into a single aggregation;

FIGS. 4(a)-4(b) are schematic diagrams in which detector blocks in the PET detection structure with application adaptability according to the disclosure are arranged in a panel mode, where FIG. 4(a) is a schematic diagram in which six detector blocks are arranged in the way that every three detector blocks are arranged in a panel mode; and FIG. 4(b) is a schematic diagram in which two detector blocks with large size are arranged in a panel mode; and FIGS. 5(a)-5(b) are schematic diagrams showing that detector blocks in a PET detection structure with application adaptability are arranged based on at least two of the five kinds of properties, according to the disclosure, where FIG.

5(a) is a schematic diagram in which two detecting blocks of which the inherent spatial resolution is level 3 and the temporal characteristic is level 1 are clustered with one detecting block of which the inherent spatial resolution is level 1 and the temporal characteristic is level 1 into one detector unit and the detector units are arranged on a detection ring in equally spaced way; and FIG. 5(b) is a schematic diagram in which the detecting units in FIG. 5(a) are arranged on the detection ring in unequally spaced way.

DETAILED DESCRIPTION

A PET detection structure and system with application adaptability are disclosed according to the disclosure. The PET detection structure and system with application adaptability reduces amount of used detector blocks of high performance level, and saves cost for establishing the system while ensuring acquirement of high quality images in a local region.

A PET detection system with application adaptability, including the foregoing PET detection structure with application adaptability, is also disclosed according to the disclosure, and the PET detection system with application adaptability further includes a detector controlling module, an image reconstruction module and a detector programming module.

Technical solutions of the embodiments of the present disclosure will be illustrated in detail with the drawings of the embodiments of the disclosure. Apparently, the described embodiments are merely a few rather than all of the embodiments of the present disclosure. Any other embodiments obtained by persons of ordinary skill in the art based on the embodiments of the present disclosure without creative efforts shall fall within the protection scope of the present disclosure.

Figure 1:
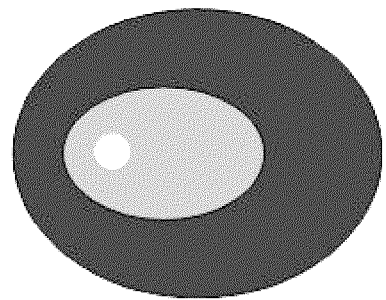
FIG. 1 shows a simulated object under detection.
Figure 2A:
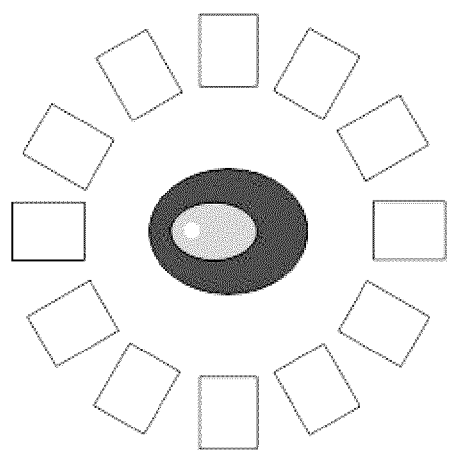
FIGS. 2(a)-2(d) are schematic diagrams of specific surrounding patterns for a PET detection structure with application adaptability, where
Figure 2B:
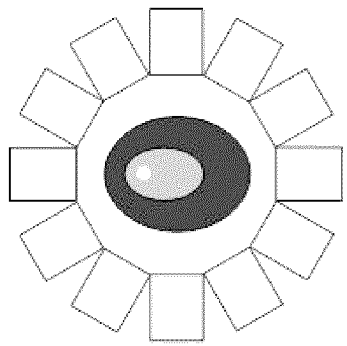
Figure 2C:
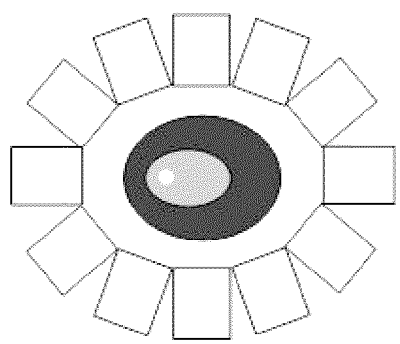
Figure 2D:
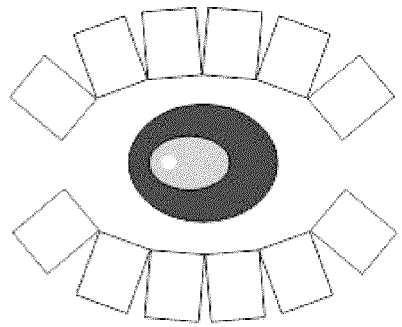

FIG. 1 shows a simulated object under detection, where the white region represents a region of interest, the light gray region represents organs/tissues where the region of interest locates, and the blackest region represents other organs/tissues in the transect of the object under detection.

The PET detection structure with application adaptability disclosed by the disclosure includes at least two detector blocks and a detection ring for disposing the detector blocks. The at least two detector blocks are arranged on the detection ring. The size of the detection ring can be adjusted according to the locations and sizes of the object under detection, the part under detection and the region of interest. The detector blocks arranged on the detection ring may have different sizes, and the geometric shape of the detector block may be an irregular cuboid, such as a frustum.

In programming layout of the PET detection structure with application adaptability according to an embodiment of the disclosure, the detector blocks are programmed, according to the position and shape of the region of interest, a structural characteristic, an imaging characteristic and an imaging performance requirement of the object under detection, and based on the performance and geometric dimensions of the detector blocks in an imaging system, to encircle the object under detection in a surrounding pattern.

With regard to the surrounding pattern, regular geometric shapes such as circle and oval may be utilized; or an irregular convex shape may be utilized; or a geometric shape similar to the object under detection may be utilized according to structural characteristic of the object under detection, for example, a shape similar to the mamma is utilized for a mammary scan.

FIG. 2 shows schematic diagrams of specific surrounding patterns for the PET detection structure with application adaptability according to the disclosure. FIG. 2(a) is a schematic diagram in which detector blocks with same size are distributed in a regular circle in an equally spaced way; FIG. 2(b) is a schematic diagram in which a radius of the detecting system can be changed and detector blocks are closely arranged in a circle; FIG. 2(c) is a schematic diagram in which detector blocks are closely arranged in an oval; FIG. 2(d) is a schematic diagram in which detector blocks are closely arranged in half arcs with two ends opened. Protection scope of claims in the disclosure covers various embodiments, for example, equally spaced arrangement (according to the specification, equally spaced arrangement indicates that two detector blocks or two detecting units are spaced from each other by a same number of detector blocks), close arrangement (according to the specification, close arrangement indicates that there is no gap between two detector blocks or two detecting units), distributed arrangement (according to the disclosure, distributed arrangement indicates that there is a gap between two detector blocks or two detecting units, and the gaps can be equal or unequal), etc. Although only four drawings of FIG. 2(a)-FIG. 2(d) are taken as examples to describe embodiments according to the disclosure, other embodiments not shown in the drawings are still within the protection scope of the disclosure.

As shown in FIG. 4, according to the embodiment of the disclosure, some of the used detector blocks may be arranged in a panel mode. A detector block arranged in a panel mode may be a combination of a plurality of detector blocks or may be a detector block with large size. FIG. 4(a) is a schematic diagram in which six detector blocks are arranged in the way that every three detector blocks are arranged in a panel mode; FIG. 4(b) is a schematic diagram in which two detector blocks with large size are arranged in a panel mode. In FIG. 4, detector blocks not arranged in the panel mode are arranged closely; of course, in other embodiments the detector blocks may be distributed in an equally spaced way or unequally spaced way, which are not enumerate here. In general, the embodiments shown in FIG. 4(a)-FIG. 4(b) according to the disclosure may not limit the protection scope of the disclosure, and other alternative embodiments all fall within the protection scope of the disclosure.

According to the embodiment of the disclosure, each detector block may have the properties including inherent spatial resolution, temporal characteristic, energy resolution, detection efficiency and a maximum counting rate. The temporal characteristic of the detector block is a contribution of the detector block to time resolution, which is a sum of contributions to the time resolution made by components including scintillation crystal, optical guide, photoelectric converter and electronics system and the like. At least one detector block in the at least two detector blocks has a higher level than other detector blocks in terms of a same property.

The detector blocks may be graded into different levels based on different application fields of the PET and different objects and parts under detection, which can not be exclusively described in the disclosure, therefore only some ways for grading the properties into levels are briefly described in the disclosure. However, the description for the specific ways for grading levels may not limit the protection scope of the disclosure, and any other ways of grading levels, not exclusively described herein, are within the protection scope of the disclosure.

Three specific ways are involved in grading levels according to the disclosure, each way includes a plurality of embodiments, and the three specific ways are described through several embodiments for each way as follows.

First Way for Property Grading

The levels of the detector blocks are graded with an equal interval, where the interval between the levels of the inherent spatial resolution is in a range of 0.1 mm-10.0 mm, the interval between the levels of the temporal characteristic is in a range of 10 ps-50 ns, the interval between the levels of the energy resolution is in a range of 3%-50%, the interval between the levels of the detection efficiency is in a range of 3%-90%, and the interval between the levels of the maximum counting rate is in a range of 10 k cps-20 M cps.

Embodiment 1

The inherent spatial resolution is graded with one level per 0.2 mm; the temporal characteristic is graded with one level per 30 ps, the energy resolution is graded with one level per 5%; the detection efficiency is graded with one level per 5%; and the maximum counting rate is graded with one level per 50 k cps.

Embodiment 2

The inherent spatial resolution is graded with one level per 0.1 mm; the temporal characteristic is graded with one level per 10 ps, the energy resolution is graded with one level per 3%; the detection efficiency is graded with one level per 3%; and the maximum counting rate is graded with one level per 10 k cps.

Embodiment 3

The inherent spatial resolution is graded with one level per 10.0 mm; the temporal characteristic is graded with one level per 50 ns, the energy resolution is graded with one level per 50%; the detection efficiency is graded with one level per 90%; and the maximum counting rate is graded with one level per 20 M cps.

Foregoing embodiments are only a few embodiments, and the embodiments do not limit the actual protection scope of the disclosure.

Second Way for Property Grading

The properties of the detector block are graded into two levels by a fixed value, where the fixed value for grading levels of the inherent spatial resolution is in a range of 0.1 mm-10.0 mm, the fixed value for grading levels of the temporal characteristic is in a range of 10 ps-50 ns, the fixed value for grading levels of the energy resolution is in a range of 3%-50%, the fixed value for grading levels of the detection efficiency is in a range of 3%-90%, and the fixed value for grading levels of the maximum counting rate is in a range of 10 k cps-20 M cps.

In this grading way, if the fixed value equals to a median value, the two levels are graded with an equal interval.

Embodiment 1

The inherent spatial resolution is graded into two levels with the value 2.0 mm as the boundary; the temporal characteristic is graded into two levels with the value 600 ps as the boundary; the energy resolution is graded into two levels with the value 15% as the boundary; the detection efficiency is graded into two levels with the value 50% as the boundary; and the maximum counting rate is graded into two levels with the value 200 k cps as the boundary.

Embodiment 2

The inherent spatial resolution is graded into two levels with the value 0.1 mm as the boundary; the temporal characteristic is graded into two levels with the value 10 ps as the boundary; the energy resolution is graded into two levels with the value 3% as the boundary; the detection efficiency is graded into two levels with the value 3% as the boundary; and the maximum counting rate is graded into two levels with the value 10 k cps as the boundary.

Embodiment 3

The inherent spatial resolution is graded into two levels with the value 10.0 mm as the boundary; the temporal characteristic is graded into two levels with the value 50 ns as the boundary; the energy resolution is graded into two levels with the value 50% as the boundary; the detection efficiency is graded into two levels with the value 90% as the boundary; and the maximum counting rate is graded into two levels with the value 20 M cps as the boundary.

Foregoing embodiments are only a few embodiments, and the embodiments do not limit the actual protection scope of the disclosure.

Third Way for Property Grading

For the properties of the detector blocks, in a case that a difference between optimal performance and worst performance of all detector blocks on the detection ring is greater than a threshold, it is determined that a level difference for the property is present.

The property may be graded according to the first or second way for property grading as follows:

In a case that the difference between the optimal performance and the worst performance of all the detector blocks is greater than a threshold, it is determined that a level difference for the property is present, where the threshold for determining the presence of level difference for the inherent spatial resolution is in a range of 0.1 mm-10.0 mm, the threshold for determining the presence of level difference for the temporal characteristic is in a range of 10 ps-50 ns, the threshold for determining the presence of level difference for the energy resolution is in a range of 3%-50%, the threshold for determining the presence of level difference for the detection efficiency is in a range of 3%-90%, and the threshold for determining the presence of level difference for the maximum counting rate is in a range of 10 k cps-20 M cps.

Embodiment 1

A threshold for determining the presence of level difference for the inherent spatial resolution is 2.0 mm, a threshold for determining the presence of level difference for the temporal characteristic is 200 ps, a threshold for determining the presence of level difference for the energy resolution is 15%, a threshold for determining the presence of level difference for the detection efficiency is 30%, and a threshold for determining the presence of level difference for the maximum counting rate is 200 k cps.

Embodiment 2

A threshold for determining the presence of level difference for the inherent spatial resolution is 0.1 mm, a threshold for determining the presence of level difference for the temporal characteristic is 10 ps, a threshold for determining the presence of level difference for the energy resolution is 3%, a threshold for determining the presence of level difference for the detection efficiency is 3%, and a threshold for determining the presence of level difference for the maximum counting rate is 10 k cps.

Embodiment 3

A threshold for determining the presence of level difference for the inherent spatial resolution is 10.0 mm, a threshold for determining the presence of level difference for the temporal characteristic is 20 ns, a threshold for determining the presence of level difference for the energy resolution is 50%, a threshold for determining the presence of level difference for the detection efficiency is 90%, and a threshold for determining the presence of level difference for the maximum counting rate is 20 M cps.

In this way of grading levels, the threshold for determining the presence of level difference for the property and the threshold for property grading may be different. Therefore ranges of the two kinds of thresholds for property grading are further limited as follows.

The levels of the detector blocks are graded with an equal interval, where the interval between the levels of the inherent spatial resolution is in a range of 0.1 mm-10.0 mm, the interval between the levels of the temporal characteristic is in a range of 10 ps-50 ns, the interval between the levels of the energy resolution is in a range of 3%-50%, the interval between the levels of the detection efficiency is in a range of 3%-90%, and the interval between the levels of the maximum counting rate is in a range of 10 k cps-20 M cps.

The properties of the detector blocks are graded into two levels by a fixed value, where the fixed value for grading levels of the inherent spatial resolution is in a range of 0.1 mm-10.0 mm, the fixed value for grading levels of the temporal characteristic is in a range of 10 ps-50 ns, the fixed value for grading levels of the energy resolution is in a range of 3%-50%, the fixed value for grading levels of the detection efficiency is in a range of 3%-90%, and the fixed value for grading levels of the maximum counting rate is in a range of 10 k cps-20 M cps.

Since the ranges of the thresholds/fixed values for the above two ways of property grading are the same, embodiments of the two ways may be coincided with each other, and several common embodiments for the two ways of property grading are selected to be described in the following.

Embodiment 1

A threshold/fixed value for grading the inherent spatial resolution is 2.0 mm; a threshold/fixed value for grading the temporal characteristic is 200 ps; a threshold/fixed value for grading the energy resolution is 15%; a threshold/fixed value for grading the detection efficiency is 30%; a threshold/fixed value for grading the maximum counting rate is 200 k cps.

Embodiment 2

A threshold/fixed value for grading the inherent spatial resolution is 0.1 mm; a threshold/fixed value for grading the temporal characteristic is 10 ps; a threshold/fixed value for grading the energy resolution is 3%; a threshold/fixed value for grading the detection efficiency is 3%; a threshold/fixed value for grading the maximum counting rate is 10 k cps.

Embodiment 3

A threshold/fixed value for grading the inherent spatial resolution is 10.0 mm; a threshold/fixed value for grading the temporal characteristic is 20 ns; a threshold/fixed value for grading the energy resolution is 50%; a threshold/fixed value for grading the detection efficiency is 90%; a threshold/fixed value for grading the maximum counting rate is 20 M cps.

The detector blocks are arranged based on one of the five kinds of properties in following ways.

(1) The detector blocks with a same level or with adjacent levels or with a plurality of different levels are arranged in a spaced way, including equally spaced or unequally spaced.

Figure 3A:
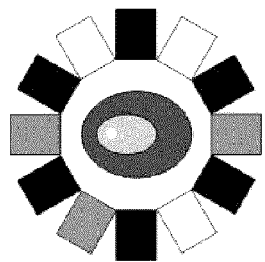
FIGS. 3(a)-3(g) are schematic diagrams showing that detector blocks in a PET detection structure with application adaptability are arranged based on one of the five kinds of properties, according to the disclosure, where
Figure 3B:
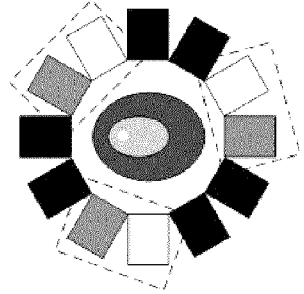
Figure 3C:
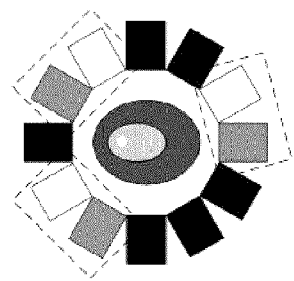
Figure 3D:
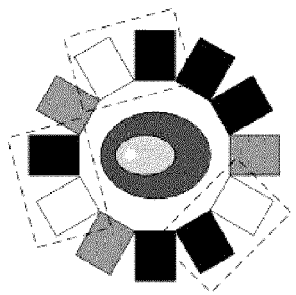
Figure 3E:
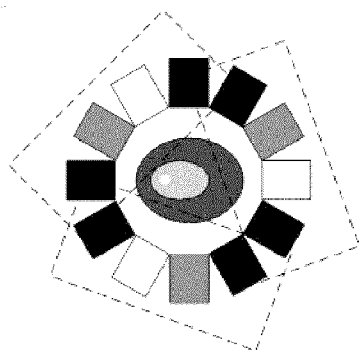

Specifically, taking the inherent spatial resolution of the detector block as an example, FIG. 3 includes schematic diagrams showing that detector blocks in a PET detection structure with application adaptability according to the disclosure are arranged based on one of the five kinds of properties. There are totally twelve detector blocks on a detection ring. Based on the first way for property grading, the inherent spatial resolution is graded into three levels: level 1, represented by a box filled with white, is the optimal performance; level 2, represented by a box filled with grey, is secondary performance; and level 3, represented by a box filled with black, is the most common performance. There are three level 1 detector blocks, three level 2 detector blocks, and six level 3 detector blocks in the twelve detector blocks. FIG. 3(a) is a schematic diagram in which detector blocks are arranged on the detection ring in the way that the level 3 detector blocks are equally spaced;

FIG. 3(b) is a schematic diagram in which detector blocks are arranged on the detection ring in the way that the level 1 and level 2 detector blocks are equally spaced; FIG. 3(c) is a schematic diagram in which detector blocks are arranged on a detection ring in the way that the level 1 and level 2 detector blocks are unequally spaced; FIG. 3(d) is a schematic diagram in which detector blocks are arranged on a detection ring in the way that the level 1 and level 3 detector blocks are unequally spaced; FIG. 3(e) is a schematic diagram in which detector blocks are arranged on a detection ring in the way that the level 1, level 2 and level 3 detector blocks are circularly arranged;

(2) The detector blocks with a same level or with adjacent levels or with a plurality of different levels are arranged in a way that sections of the detector blocks are clustered into a single aggregation or a plurality of aggregations. The plurality of aggregations may include the same or different number of detector blocks.

Figure 3F:
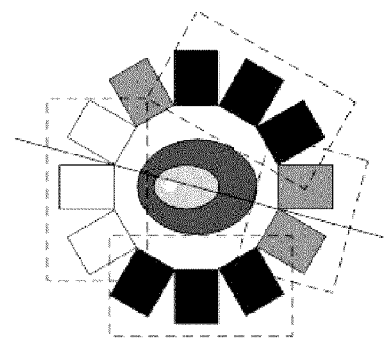
Figure 3G:
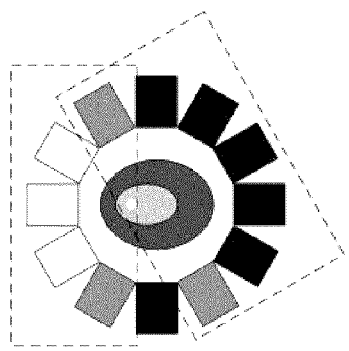

Specially, as shown in FIG. 3(f)-FIG. 3(g), FIG. 3(f) is a schematic diagram in which detector blocks are arranged on a detection ring in a way that the level 1, level 2 and level 3 detector blocks are clustered into a single aggregation or a plurality of aggregations.

As shown in FIG. 3(f), the level 1 detector blocks may clustered into a single aggregation, and the aggregation includes all the level 1 detector blocks; alternatively, the level 2 detector blocks may clustered into a single aggregation, the aggregation includes two level 2 detector blocks and the remaining one level 2 detector block is arranged on the detection ring arbitrarily; alternatively, the level 3 detector blocks may clustered into two aggregation, and each aggregation includes three level 3 detector blocks; alternatively, the detector blocks in two different levels (levels 1 and 2, levels 1 and 3, or levels 2 and 3) or three different levels may be clustered into a plurality of aggregations. FIG. 3(g) is a schematic diagram in which detector blocks are arranged on a detection ring in a way that the level 1 and level 2 detector blocks are clustered into a single aggregation or in a way that the level 2 and level 3 detector blocks are clustered into a single aggregation. The arrangement in FIG. 3(g) may be considered as the arrangement that level 1 and level 2 detector blocks are clustered into a single aggregation and the aggregation includes all the level 1 detector blocks and two level 2 detect blocks, or may be considered as the arrangement that level 2 and level 3 detector blocks are clustered into a single aggregation.

In the FIGS. 3(a)-3(g), the detector blocks are arranged closely; of course, in other embodiments, the detector blocks may be arranged closely or distributed, mainly depending on radius and shape of the detector system and size and shape of the detector blocks.

In the FIGS. 3(a)-3(g), the detector blocks are arranged closely; of course, in other embodiments, the detector blocks may be arranged closely or distributed, mainly depending on radius and shape of the detector system and size and shape of the detector blocks. The protection scope of the disclosure is not limited by the arrangement of the detector blocks shown in FIG. 3(a)-FIG. 3(e), and all other embodiments of the arrangement of the detector blocks are within the protection scope of the disclosure.

The illustration in FIGS. 3(a)-3(g) that twelve detector blocks are arranged on the detection ring is exemplary, the protection scope of the disclosure is not limited by the number of the detector blocks, and any other arrangements of more than two detector blocks are within the protection scope of the disclosure.

According to the disclosure, each of the plurality of aggregations functions as one detecting unit, and the plurality of detecting units may be arranged on the detection ring in a symmetric way, in a way that some are arranged closely and some are distributed, or in a spaced way, which are not shown in the drawings herein. Any arrangements of the detecting units are within the protection scope of the disclosure. As shown in FIG. 3(f), the level 3 detector blocks are clustered into two aggregations, and the two detecting units are arranged on the detection ring in an unequally spaced way, or it may be considered that the two detecting units are in a symmetric arrangement about a line passing through the center of the detection ring.

The arrangements shown in FIG. 3(a)-FIG. 3(g) may be interpreted in various ways and the embodiments of the arrangement are not limited to a single interpretation.

FIG. 5 includes schematic diagrams showing that detector blocks in a PET detection structure with application adaptability are arranged based on at least two of the five kinds of properties, according to the disclosure. In FIG. 5, two kinds of properties, i.e., inherent spatial resolution and temporal characteristic of detector blocks are taken for example. There are totally twelve detector blocks on the detection ring. Based on the first way for property grading, the inherent spatial resolution of the detector blocks is graded into three levels: level 1, represented by a box filled with white, is the optimal performance; level 2, represented by a box filled with grey, is secondary performance; and level 3, represented by a box filled with black, is the most common performance. According to the second way for property grading, the temporal characteristic of the detector blocks is graded into two levels: level 1, represented by a box filled with oblique lines, is high performance; and level 2, represented by a box filled with crosses, is low performance. There are two detector blocks of which the inherent spatial resolution is level 1 and the temporal characteristic is also level 1, four detector blocks of which the inherent spatial resolution is level 2 and the temporal characteristic is also level 2, and six remaining detector blocks of which the inherent spatial resolution is level 3 while the temporal characteristic is level 1.

As shown in FIG. 5, the detector blocks are arranged based on at least two of the five kinds of properties in the following ways.

(1) Detector blocks with an arbitrary level or with adjacent levels or with a plurality of different levels in terms of the plurality of properties are clustered into one detecting unit, and the detecting units are arranged in a spaced way, including equally spaced or unequally space.

FIG. 5(a) is a schematic diagram in which two detecting blocks of which the inherent spatial resolution is level 3 and the temporal characteristic is level 1 are clustered with one detecting block of which the inherent spatial resolution is level 1 and the temporal characteristic is level 1 into one detector unit and the detector units are arranged on a detection ring in equally spaced way. FIG. 5(b) is a schematic diagram in which the detecting units in FIG. 5(a) are arranged on the detection ring in unequally spaced way.

(2) Detector blocks with an arbitrary level or with adjacent levels or with a plurality of different levels in terms of the plurality of properties are clustered as one detecting unit; and detecting units are arranged in a way that sections of the detector units are clustered into a single aggregation or a plurality of aggregations. The plurality of aggregations may include the same or different number of detector blocks.

Specifically, as shown in FIG. 5(a) and FIG. 5(b), the detecting units are clustered as two aggregations, and the two aggregations include the same number of detector blocks.

In the FIG. 5(a)-FIG. 5(b), all detector blocks are arranged closely; of course, in other embodiments, the detector blocks may be arranged in a dispersive way, or arranged in a close way or dispersive way, mainly depending on radius and shape of the detector system and size and shape of the detector blocks. The protection scope of the disclosure is not limited by the arrangement of the detector blocks shown in FIG. 5(a)-FIG. 5(b), and all other embodiments of the arrangement of the detector blocks are within the protection scope of the disclosure.

The arrangements shown in FIG. 5(a)-FIG. 5(b) may be interpreted in various ways and the embodiments of the arrangement are not limited to a single interpretation.

The illustration in FIG. 5(a)-FIG. 5(b) that twelve detector blocks are arranged on the detection ring is exemplary, the protection scope of the disclosure is not limited by the number of the detector blocks, and any other arrangements of more than two detector blocks are within the protection scope of the disclosure.

The detecting units are arranged on the detection ring in a symmetric way, in a way that some are arranged closely and some are distributed, or in a spaced way.

Detector blocks clustered into a plurality of aggregations may be arranged on the detection ring in various symmetric ways, and the aggregations of the clustered detector blocks may include the same or different number of detector blocks. The symmetry is implemented with taking the center of the aggregated detector blocks on the transect as a reference point. The patterns for the symmetry include:

A) a symmetry with respect to a certain center;

B) a symmetry with respect to a symmetry axis which is a straight line through a certain center, and the symmetry axis may be:

(a) a straight line defined by the reference point of a aggregated or un-aggregated detector block and the center, or (b) a straight line defined by two centers, in which the center is a center of the detection ring, or a center of the region of interest, or a center of a portion region of the region of interest, or a center of the object under detection. The center may be a geometric center or a center of gravity.

C) a symmetry with respect to a line connecting reference points of two aggregated or un-aggregated detector blocks or reference points of one aggregated detector block and one un-aggregated detector block.

In the PET detection structure and system with application adaptability according to the embodiments of the disclosure, detector blocks of different performance levels cooperate with each other; and by optimizing the arrangement of the detector blocks, the used amount of detector blocks of high performance level is reduced while ensuring quality of the acquired images, and cost for establishing the system is saved.

Those of ordinary skills in the art will appreciate that the disclosure is not limited to the details of above exemplary embodiments and may be realized with other specific forms without departing from the spirit and basic features of the disclosure. Hence, the embodiments should be considered in any case as exemplary rather than limiting, and the scope of the disclosure is defined by the claims but not the above description. Therefore, the disclosure is meant to include all changes within the contents and equivalence of the claims. of the reference numerals in the claims should not be seen as a limitation to the claims.

In addition, it should be understood that although the specification is described with reference to several embodiments, not every embodiment forms an independent technical solution. The arrangement of the specification is merely for purpose of clarity. Those of ordinary skills in the art should take the specification as a whole, and technical solutions in the embodiments may be properly combined to form other understandable embodiments.

The invention claimed is:

1. A positron emission tomography detection structure with application adaptability, comprising at least two detector blocks and a single detection ring for disposing the detector blocks,
    wherein the at least two detector blocks are arranged on the single detection ring and surround an object under detection, each detector block has properties comprising inherent spatial resolution, temporal characteristic, energy resolution, detection efficiency and maximum counting rate, and
    wherein the properties of the detector block are graded into a plurality of levels, and at least one detector block in the at least two detector blocks has a higher level than other detector blocks in terms of a same property.

2. The positron emission tomography detection structure with application adaptability according to claim 1, wherein the surrounding is in a regular geometric shape, or in an irregular convex shape, or in a geometric shape similar to that of the object under detection according to structural characteristic of the object under detection.

3. The positron emission tomography detection structure with application adaptability according to claim 1, wherein the levels of the detector blocks are graded with an equal interval, wherein the interval between the levels of the inherent spatial resolution is in a range of 0.1 mm-10.0 mm, the interval between the levels of the temporal characteristic is in a range of 10 ps-50 ns, the interval between the levels of the energy resolution is in a range of 3%-50%, the interval between the levels of the detection efficiency is in a range of 3%-90%, and the interval between the levels of the maximum counting rate is in a range of 10 k cps-20 M cps.

4. The positron emission tomography detection structure with application adaptability according to claim 1, wherein the properties of the detector block are graded into two levels by a fixed value, wherein the fixed value for grading levels of the inherent spatial resolution is in a range of 0.1 mm-10.0 mm, the fixed value for grading levels of the temporal characteristic is in a range of 10 ps-50 ns, the fixed value for grading levels of the energy resolution is in a range of 3%-50%, the fixed value for grading levels of the detection efficiency is in a range of 3%-90%, and the fixed value for grading levels of the maximum counting rate is in a range of 10 k cps-20 M cps.

5. The positron emission tomography detection structure with application adaptability according to claim 1, wherein in a case that a difference between optimal performance and worst performance of all the detector blocks is greater than a threshold, it is determined that a level difference for the property is present, wherein the threshold for determining the presence of level difference for the inherent spatial resolution is in a range of 0.1 mm-10.0 mm, the threshold for determining the presence of level difference for the temporal characteristic is in a range of 10 ps-50 ns, the threshold for determining the presence of level difference for the energy resolution is in a range of 3%-50%, the threshold for determining the presence of level difference for the detection efficiency is in a range of 3%-90%, and the threshold for determining the presence of level difference for the maximum counting rate is in a range of 10 k cps-20 M cps.

6. The positron emission tomography detection structure with application adaptability according to claim 5, wherein the levels of the detector blocks are graded with an equal interval, wherein the interval between the levels of the inherent spatial resolution is in a range of 0.1 mm-10.0 mm, the interval between the levels of the temporal characteristic is in a range of 10 ps-50 ns, the interval between the levels of the energy resolution is in a range of 3%-50%, the interval between the levels of the detection efficiency is in a range of 3%-90%, and the interval between the levels of the maximum counting rate is in a range of 10 k cps-20 M cps.

7. The positron emission tomography detection structure with application adaptability according to claim 5, wherein the properties of the detector block are graded into two levels by a fixed value, wherein the fixed value for grading levels of the inherent spatial resolution is in a range of 0.1 mm-10.0 mm, the fixed value for grading levels of the temporal characteristic is in a range of 10 ps-50 ns, the fixed value for grading levels of the energy resolution is in a range of 3%-50%, the fixed value for grading levels of the detection efficiency is in a range of 3%-90%, and the fixed value for grading levels of the maximum counting rate is in a range of 10 k cps-20 M cps.

8. The positron emission tomography detection structure with application adaptability according to claim 1, wherein the detector blocks are arranged based on one of the five kinds of properties in the following ways:
    (1) detector blocks with a same level or with adjacent levels or with a plurality of different levels are arranged in a spaced way;
    (2) detector blocks with a same level or with adjacent levels or with a plurality of different levels are arranged in a way that sections of the detector blocks are clustered into a single aggregation or a plurality of aggregations.

9. The positron emission tomography detection structure with application adaptability according to claim 8, wherein each of the plurality of aggregations functions as one detecting unit, the plurality of detecting units are arranged on the single detection ring in a symmetric way, in a way that some are arranged closely and some are distributed, or in a spaced way.

10. The positron emission tomography detection structure with application adaptability according to claim 1, wherein the detector blocks are arranged based on at least two of the five kinds of properties in ways comprising:
    (1) detector blocks with an arbitrary level or with adjacent levels or with a plurality of different levels in terms of the plurality of properties are clustered as one detecting unit, and the detecting units are arranged in a spaced way;
    (2) detector blocks with an arbitrary level or with adjacent levels or with a plurality of different levels in terms of the plurality of properties are clustered as one detecting unit, and the detecting units are arranged in a way that sections of the detector blocks are clustered into a single aggregation or a plurality of aggregations.

11. The positron emission tomography detection structure with application adaptability according to claim 10, wherein the plurality of detecting units are arranged on the single detection ring in a symmetric way, in a way that some are arranged closely and some are distributed, or in a spaced way.

12. A positron emission tomography detection system with application adaptability, comprising a positron emission tomography detection structure with application adaptability, a detector controlling module, an image reconstruction module and a detector programming module, wherein the positron emission tomography detection structure with application adaptability comprises at least two detector blocks and a single detection ring for disposing the detector blocks, the at least two detector blocks are arranged on the single detection ring and surround an object under detection, each detector block has properties comprising inherent spatial resolution, temporal characteristic, energy resolution, detection efficiency and maximum counting rate, wherein the properties of the detector block are graded into a plurality of levels, and at least one detector block in the at least two detector blocks has a higher level than other detector blocks in terms of a same property.

* * * * *